(12) United States Patent
Schwab

(10) Patent No.: US 8,663,289 B2
(45) Date of Patent: Mar. 4, 2014

(54) PEDICLE SCREW HEAD EXTENDER

(75) Inventor: Frank J. Schwab, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1159 days.

(21) Appl. No.: 12/608,205

(22) Filed: Oct. 29, 2009

(65) Prior Publication Data

US 2011/0106178 A1    May 5, 2011

(51) Int. Cl.
*A61B 17/70* (2006.01)

(52) U.S. Cl.
USPC ............................................ 606/267; 606/266

(58) Field of Classification Search
USPC ................. 606/319, 60, 246–279, 305–308
See application file for complete search history.

(56) References Cited

U.S. PATENT DOCUMENTS

| | | | |
|---|---|---|---|
| 5,443,467 A * | 8/1995 | Biedermann et al. | 606/65 |
| 5,733,286 A | 3/1998 | Errico et al. | |
| 5,782,831 A | 7/1998 | Sherman et al. | |
| 5,964,760 A * | 10/1999 | Richelsoph | 606/279 |
| 6,478,795 B1 | 11/2002 | Gournay et al. | |
| 6,565,565 B1 * | 5/2003 | Yuan et al. | 606/272 |
| 6,626,908 B2 * | 9/2003 | Cooper et al. | 606/266 |
| 7,018,379 B2 | 3/2006 | Drewry et al. | |
| 7,470,279 B2 | 12/2008 | Jackson | |
| 2001/0001119 A1 * | 5/2001 | Lombardo | 606/73 |
| 2005/0203516 A1 | 9/2005 | Biedermann et al. | |
| 2006/0058794 A1 | 3/2006 | Jackson | |
| 2007/0055241 A1 | 3/2007 | Matthis et al. | |
| 2007/0093817 A1 | 4/2007 | Barrus et al. | |
| 2008/0086131 A1 | 4/2008 | Daly et al. | |
| 2008/0119849 A1 | 5/2008 | Beardsley et al. | |
| 2008/0249570 A1 | 10/2008 | Carson et al. | |
| 2009/0012567 A1 | 1/2009 | Biedermann et al. | |

* cited by examiner

*Primary Examiner* — Kevin T Truong
*Assistant Examiner* — Michael Araj

(57) ABSTRACT

The present invention relates to pedicle screw spinal rod connectors and more specifically, a pedicle screw head extender for use with a pedicle screw to ease connection to a spinal rod. The pedicle screw head extenders provided herein can be used with either fixed head pedicle screws or multi-axial head pedicle screws. The pedicle screw head extenders can either be threaded to or snapped into place within the various pedicle screws. It may also be possible to use the present invention with other types of spinal screws that may be connected to spinal rods without the screw actually being implanted through the pedicle of the spine.

20 Claims, 6 Drawing Sheets

PEDICLE SCREW HEAD EXTENDER

FIELD OF THE INVENTION

The present invention relates to pedicle screw spinal rod connectors and more specifically, a pedicle screw head extender for use with a pedicle screw to ease connection to a spinal rod. It may also be possible to use the extenders with other spinal screw—rod connectors.

BACKGROUND OF THE INVENTION

Spinal surgeons often treat spinal disorders with spinal fusion augmented with elongate spinal rods connected to the spine with pedicle screws or other spinal screws. Such "rod assemblies" generally comprise one or two spinal rods and a plurality of screws inserted through the pedicles and into their respective vertebral bodies. The screws are provided with connectors for coupling the spinal rods to the screws. The spinal rods extend along the longitudinal axis of the spine, coupling to the plurality of screws via their connectors.

In some cases after installing all of the pedicle screws through the pedicles the connectors do not line up properly to satisfactorily install a rod within such connectors. In these cases a surgeon will attempt to align the connectors by trying to adjust the position of the vertebrae; however, this is not always possible without danger to the patient's spine. A surgeon will often times attempt to bend the rod to make it fit within all of the connectors of the pedicle screws to properly install the rod within the connectors, however, again this can sometimes be very difficult to accomplish.

Therefore, it would be desirable to have a spacer or pedicle screw head extender device which could be added to either a fixed head or multi-axial head pedicle screw to make it easier to properly align the rod within the plurality of screws extending along the longitudinal axis of the spine. The extenders could also be used with other spinal screws not necessarily being threaded through the pedicle to assist in connecting the screw to a rod assembly.

SUMMARY OF THE INVENTION

In one embodiment, the present invention provides a pedicle head screw extender for use with a fixed head pedicle screw for connecting the pedicle screw to a spinal rod. In this embodiment, the pedicle screw being used is a fixed head screw having an elongated stem with a distal threaded portion and a proximal fixed head portion. As generally referred to herein, distal and proximal directions refer to those portions of the devices closest to and farthest away from the spinal column of a patient, respectively. The head includes a pair of oppositely positioned internally threaded branches defining a slot for receiving a spinal rod therebetween. A set screw would normally be used to capture the rod within the internally threaded slot. However, before the spinal rod is placed within the pedicle screw, the pedicle head screw extender of the present invention will be used instead. The extender has a distal threaded portion that is threadably received within the internally threaded branches of the fixed head screw. The extender has an axially extending pair of oppositely positioned internally threaded branches defining a slot for receiving the spinal rod therebetween. The set screw is then used to capture the rod with the internally threaded slot of the pedicle screw head extender to capture the rod within the extender and to the fixed head pedicle screw.

In another embodiment, a pedicle screw head extender is provided that has a distally extending post having concentric rings thereon for use with a fixed head pedicle screw. The extender further includes an axially extending pair of oppositely positioned internally threaded branches defining a slot for receiving a spinal rod therebetween. In this embodiment, once the fixed head pedicle screw is positioned within the vertebra of the spinal column, the distally extending post of the pedicle screw head extender can be snapped into place within the slot of the fixed head pedicle screw via the concentric rings positioned about the post. The spinal rod can then be placed within the slot of the pedicle screw head extender. A set screw can be used to capture the spinal rod within the slot of the pedicle screw head extender.

In another embodiment, a pedicle screw head extender can be used with a multi-axial head pedicle screw. Typically, a multi-axial pedicle screw has an elongated stem with a distal threaded portion at one end and a proximally positioned ball portion at the other end. A head portion is received about the ball portion and includes a crown positioned adjacent the ball portion of the stem within the head portion. The head further includes an axially extending pair of oppositely positioned internally threaded branches defining a slot for receiving a spinal rod therebetween. A set screw would normally capture the spinal rod within the slot of the head. This type of pedicle screw is called a multi-axial head pedicle screw because before installation of the rod and set screw, the head can freely rotate about the ball of the elongated stem. However, once the spinal rod is captured within the slot of the head by the set screw, the rod is firmly pressed against the crown which then firmly captures the ball of the elongated stem within the head to prevent further movement of the head with respect to the elongated stem of the multi-axial pedicle screw. The pedicle screw head extender for use with a multi-axial screw has an intermediate threaded portion, a distal extension extending beyond the threaded portion, and has a proximally extending pair of oppositely positioned internally threaded branches defining a slot for receiving the spinal rod there between. The distal extension extends sufficiently beyond the intermediate threaded portion such that when the pedicle screw head extender is threaded into the multi-axial pedicle screw, the distal extension contacts and biases the crown against the ball of the elongated stem to prevent further movement of the head with respect to the elongated stem of the multi-axial pedicle screw. A set screw is then used to capture the rod within the internally threaded slot of the pedicle screw head extender to capture the rod within the extender and to the multi-axial head pedicle screw. In this embodiment, the intermediate threaded portion could instead have a series of concentric rings placed around the portion to allow for a snap fit into the head of the multi-axial screw as discussed above in relation to the fixed head pedicle screw.

In yet another embodiment, a pedicle screw head extender can be used with a multi-axial head pedicle screw. In this embodiment of the pedicle screw head extender, the extender has a distal threaded portion and a proximally extending pair of oppositely positioned internally threaded branches defining a slot for receiving the spinal rod therebetween. The extender is further provided with an axial bore extending longitudinally through the extender. A piston is provided within the bore having a distal extension extending beyond the end of the distal threaded portion and a proximal end configured to abut a rod when a rod is positioned within the slot of the extender. The distal extension extends sufficiently beyond the distal threaded portion such that when the pedicle screw head extender is threaded into the multi-axial pedicle screw the distal extension contacts the crown without significant pressure to bias the crown against the ball of the elongated stem at his point. However, when a spinal rod is placed within the slot of the extender and a set screw is threaded into the internally threaded branches of the extender, the rod pushes against the piston to bias the crown against the ball of the elongated stem to prevent further movement of the head with respect to the elongated stem of the multi-axial pedicle screw.

In still other embodiments, different forms and applications of the present invention are envisioned. It would be desirable to provide a plurality of pedicle screw head extenders all having different cylindrical body lengths such that a surgeon user would be able to select which pedicle screw head extender would best fit the space needed to span the distance from the implanted pedicle screw and the rod to be installed therein within the overall spinal construct. It may also be desirable to use the present invention with other types of spinal screws that may be connected to spinal rods without the screw actually being implanted through the pedicle of the spine.

Further embodiments, forms, features, aspects, benefits, objects and advantages of the present invention shall become apparent from the detailed description and figures provided herewith.

DESCRIPTION OF THE ILLUSTRATED EMBODIMENTS

Figure 1:
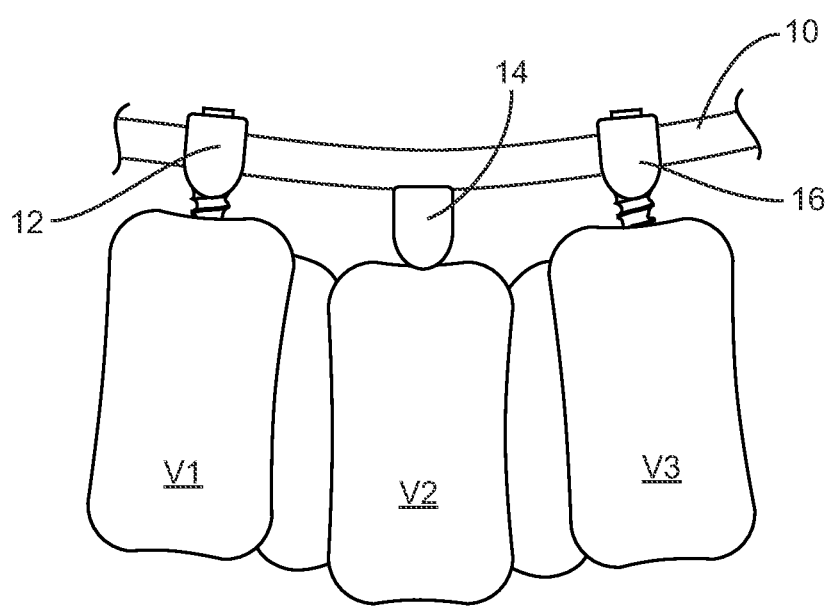
FIG. 1 is a side view of the spinal column of a patient having several pedicle screws installed therein with a spinal rod running therebetween.

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices and described methods, and any such further applications of the principles of the invention as illustrated herein are contemplated as would normally occur to one skilled in the art to which the invention relates.

Figure 9:
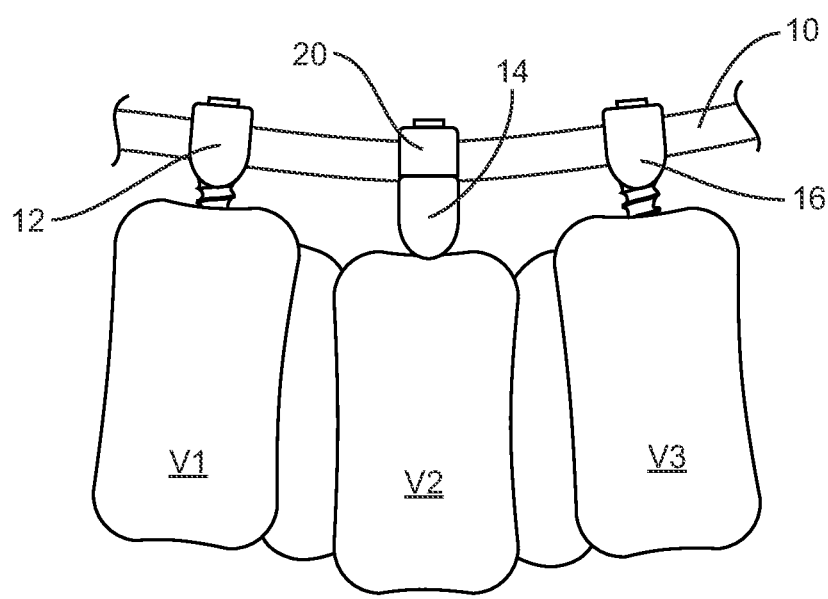
FIG. 9 is a side view of the spinal column illustrated in FIG. 1 with the pedicle screw head extender shown attached to a pedicle screw within a multiple pedicle screw construct.

FIG. 1 shows a portion of the spinal column with vertebrae V1, V2 and V3. A single rod construct is shown with rod 10 being connected to pedicle screws 12 and 16 which have been implanted in vertebrae V1 and V3, respectively. A middle pedicle screw 14 threaded into vertebra V2 is shown below rod 10 in a position where it would be very difficult to connect the pedicle screw 14 to the rod 10. This is one situation where the pedicle screw head extender of the present invention would be useful to allow for proper connection of the pedicle screw to the rod. As can be seen in FIGS. 1 and 9, the axial length of the needed pedicle screw head extender would only be determined during the spinal surgery operation. Therefore, it would be desirable to provide a plurality of pedicle screw head extenders having different axial lengths to allow for the surgeon to select the appropriate size pedicle screw head extender that would be needed in the specific application.

Figure 2:
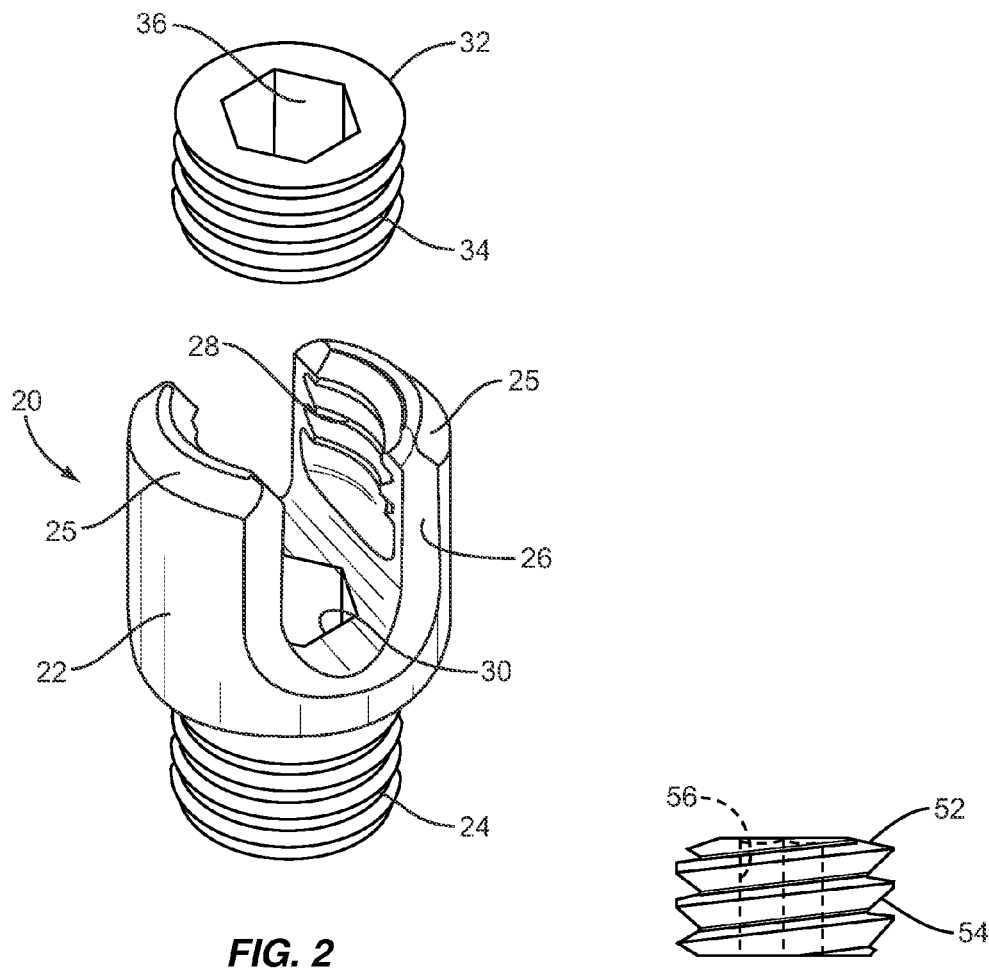
FIG. 2 is a perspective exploded view of one embodiment of the pedicle screw head extender of the present invention.

FIG. 2 shows one embodiment of the pedicle screw head extender of the present invention. The pedicle screw head extender is shown at 20 and includes a generally cylindrical body 22 having a distally extending threaded portion 24. The extender body 22 further has a pair of proximally extending branches 25 forming a slot 26 therebetween. The branches are provided with internal threads 28 configured to receive a set screw 32. The body 22 further includes an axial hexangular hole 30 in the bottom of the slot 26. The hexangular hole 30 is configured to receive a screw driver having a matching configuration to allow for the installation of the pedicle screw head extender onto a pedicle screw. The set screw 32 is provided with external threads 34 matching the threads 28 of the pedicle screw head extender 20. The set screw 32 is further provided with a hexangular hole 36 for receiving a screw driver to allow for installation of the set screw 32 to the extender 20. The holes 30 and 36 can actually be of any configuration that would match a appropriate driver to allow for the installation of the extender 20 onto a pedicle screw and the set screw 32 into the extender 20, such alternate configurations being well known in the industry.

Figure 3:
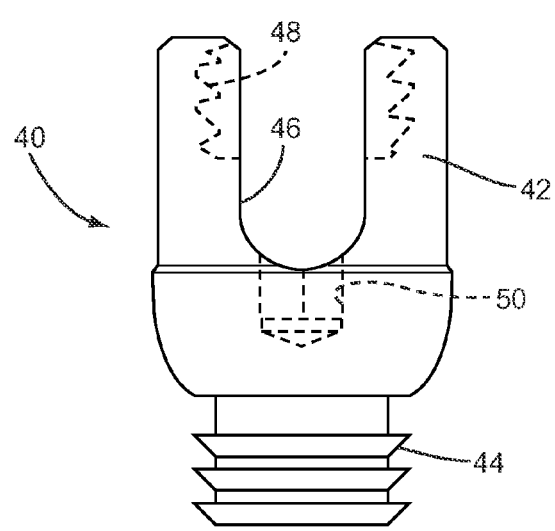
FIG. 3 is a side plan exploded view of the pedicle screw head extender illustrated in FIG. 2.

FIG. 3 shows another embodiment of the pedicle screw head extender of the present invention. The pedicle screw head extender is shown at 40 and includes a generally cylindrical body 42 having a distally extending post which is provided with a plurality of concentric rings 44 about the post to provide a snap fit connection with a typical pedicle screw. The body 42 further having a slot formed therein at 46 to provide a pair of proximally extending internally threaded branches shown at 48 and configured to receive a set screw 52. The body 42 further includes an axial hexangular hole 50 in the bottom of slot 46. The hexangular hole 50 is configured to receive a driver having a matching configuration to allow for the installation of the pedicle screw head extender onto a pedicle screw. In this embodiment, this would be accomplished by use of an axial pushing force onto the extender in a distal direction to snap fit the extender onto a pedicle screw.

Figure 4:
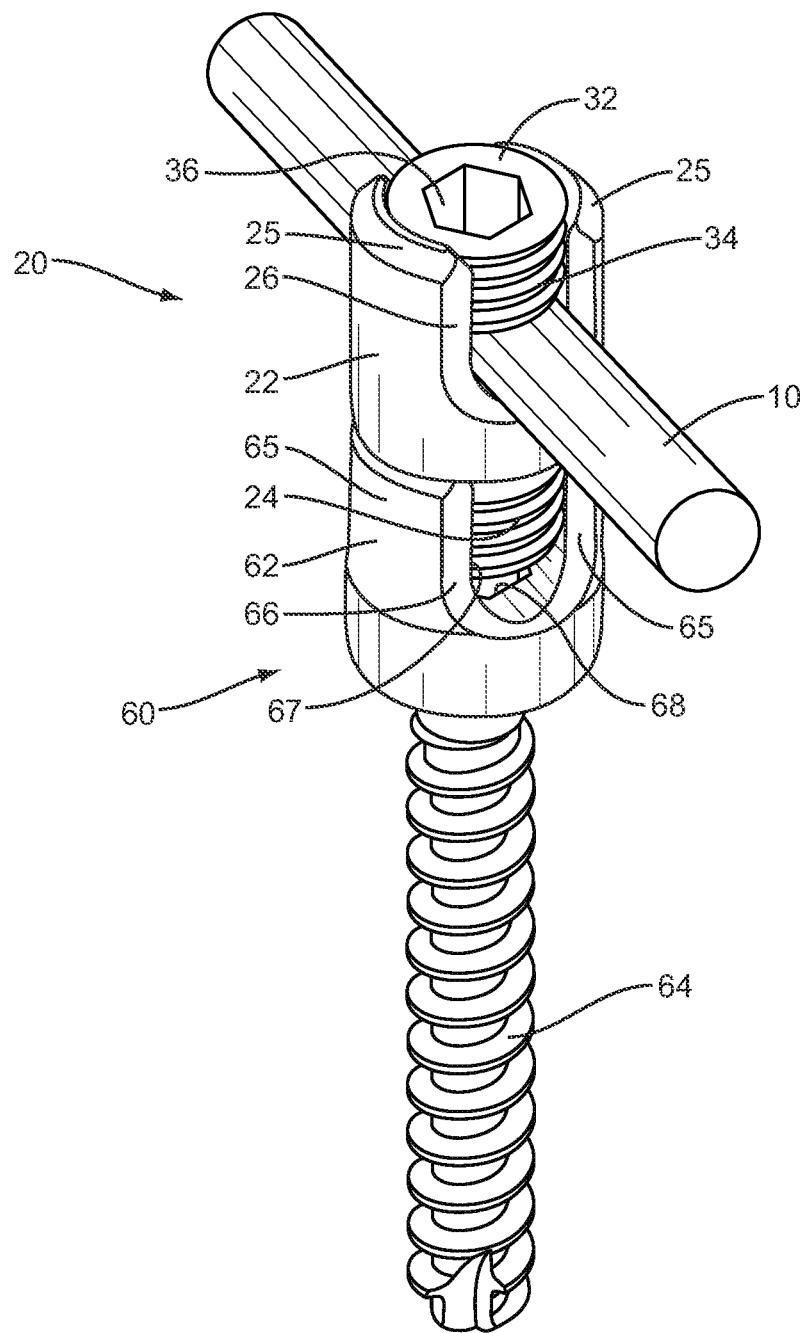
FIG. 4 is a perspective view of a pedicle screw with the pedicle screw head extender illustrated in FIG. 2 positioned thereon with a spinal rod attached thereto.

With reference to FIG. 4, there is illustrated the pedicle screw head extender 20 of FIG. 2, installed on a typical fixed head pedicle screw, generally referred to as 60. A fixed head pedicle screw 60 is shown having an elongated stem which is threaded as shown at 64 for attachment to a bone segment. The screw 60 is also provided with a generally cylindrical head 62 having a pair of proximally extending oppositely opposed branches 65 forming a slot 66 therebetween. The opposed branches 65 are internally threaded at 67 which would normally receive a set screw, however in the present invention will receive the pedicle screw head extender 20. The pedicle screw 60 would also have a hexangular hole 68 configured to receiver a screw driver having a matching configuration to allow for the installation of the pedicle screw into a bone segment of the human body. As further shown in FIG. 4, the pedicle screw head extender 20 is shown in place connected to the pedicle screw 60. The distally threaded extended portion 24 of the pedicle screw head extender 20 is received within the slot 66 of the pedicle screw 60. A rod 10 is shown in place within the slot 26 and a set screw 32 is shown threaded between the branches 25 capturing the rod 10 within the slot 26 of the pedicle screw head extender to fix the rod 10 to the pedicle screw 60. The pedicle screw head extender 40 of FIG. 3 could also be shown in place in FIG. 4 for connecting the rod 10 to the fixed head pedicle screw 60.

Figure 5:
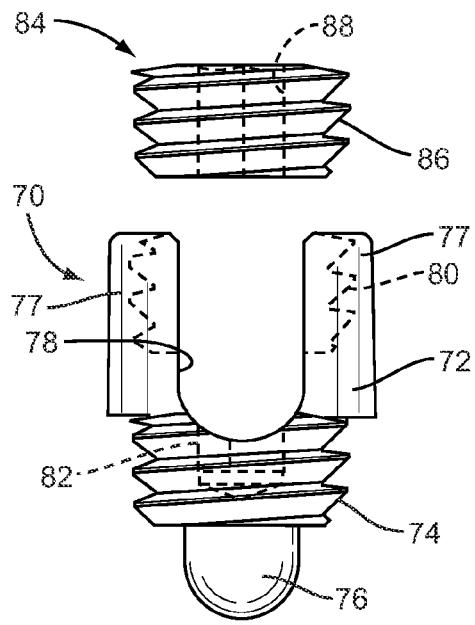
FIG. 5 is a side plan exploded view of another embodiment of the pedicle screw head extender of the present invention.
Figure 6:
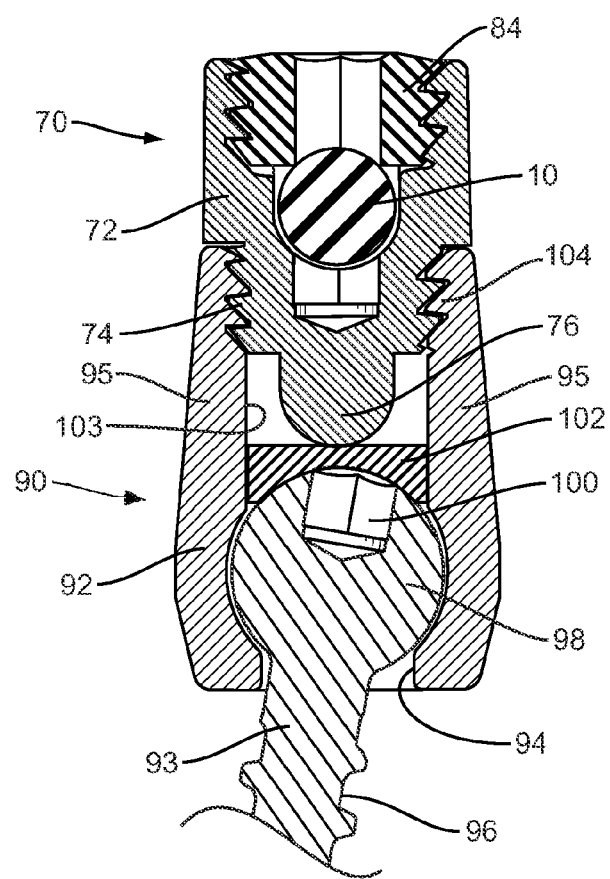
FIG. 6 is side cross sectional view of a multi-axial pedicle screw with the pedicle screw head extender illustrated in FIG. 5 installed thereon with a spinal rod attached thereto.

FIGS. 5 and 6 show another embodiment of the pedicle screw head extender of the present invention. In this embodiment, the pedicle screw head extender 70 is connected to a multi-axial head pedicle screw 90. A multi-axial pedicle screw 90 is well known in the industry. Typically, such a pedicle screw has an elongated stem 93 which is threaded at its distal end, as shown at 96, and a ball portion 98 at its proximal end. A head portion 92 is received about the ball portion 98 and includes a crown 102 positioned on the top of the ball portion 98. The elongated stem extends down below the head through a hole 94 provided in the bottom of the head portion 92.

In the industry, such multi-axial screws can have the threaded elongated stem 93 which is either top loaded through the head or bottom loaded through the bottom of the head. For ease of description, a top loaded stem and head arrangement is shown, however, both such multi-axial screws operate in the same manner. A bottom loaded stem and head arrangement would simply have a head with a larger bottom hole and use a snap ring to hold the proximal ball of the stem within the head.

As shown in FIG. 6, the head 92 further includes an axially extending pair of oppositely positioned branches 95 forming a slot 103. The branches 95 are internally threaded as shown at 104. The slot would normally receive a spinal rod therein which would be captured in place by a set screw. In operation, the head 92 is free to rotate about the ball 98 of the pedicle screw to allow for easier attachment of a spinal rod to the pedicle screw. Once the rod is positioned within the slot 103 a set screw would be used to secure the rod within the slot. The rod would push down upon the crown 102 which in turn would lock the ball 98 within the head 92 to prevent further movement of the head with respect to the threaded elongated stem 93 of the pedicle screw.

Referring back to FIG. 5, the pedicle screw head extender 70 of the present invention, is shown having a generally cylindrical body 72 with an intermediate portion which is externally threaded as shown at 74, a distally extending portion terminating in a spherical knob 76, and a proximally extending pair of oppositely positioned branches 77 which are internally threaded as shown at 80. A slot 78 is formed between the branches 77 for receiving a spinal rod therebetween. An axially extending hexangular hole 82 is provided in the bottom of the slot 78 which is configured to receive a screw driver having a matching configuration to allow for the installation of the pedicle screw head extender 70 onto the multi-axial pedicle screw 90. A set screw 84 is provided having external threads 86 and an axially extending hexangular hole 88 for receiving a screw driver to allow for installation of the set screw 84 to the extender 70.

Referring now back to FIG. 6, the pedicle screw head extender 70 is shown in position attached to the multi-axial pedicle screw 90. The external threads 74 of the intermediate portion of the extender 70 are shown in engagement with the internal threads 104 of the head 92 of the multi-axial pedicle screw 90. Once fully seated within the head, the spherical knob 76 of the extender 70 will contact and bias the crown 102 against the ball 98 of the pedicle screw to lock the head against any further movement with respect to the elongated stem 93 of the pedicle screw. A spinal rod 10 can then be placed within the slot 78 of the pedicle screw head extender 70 and the set screw 84 will be used to capture the rod 10 within the slot 78 to lock all of the components of the spinal construct together.

Figures 7, 8:
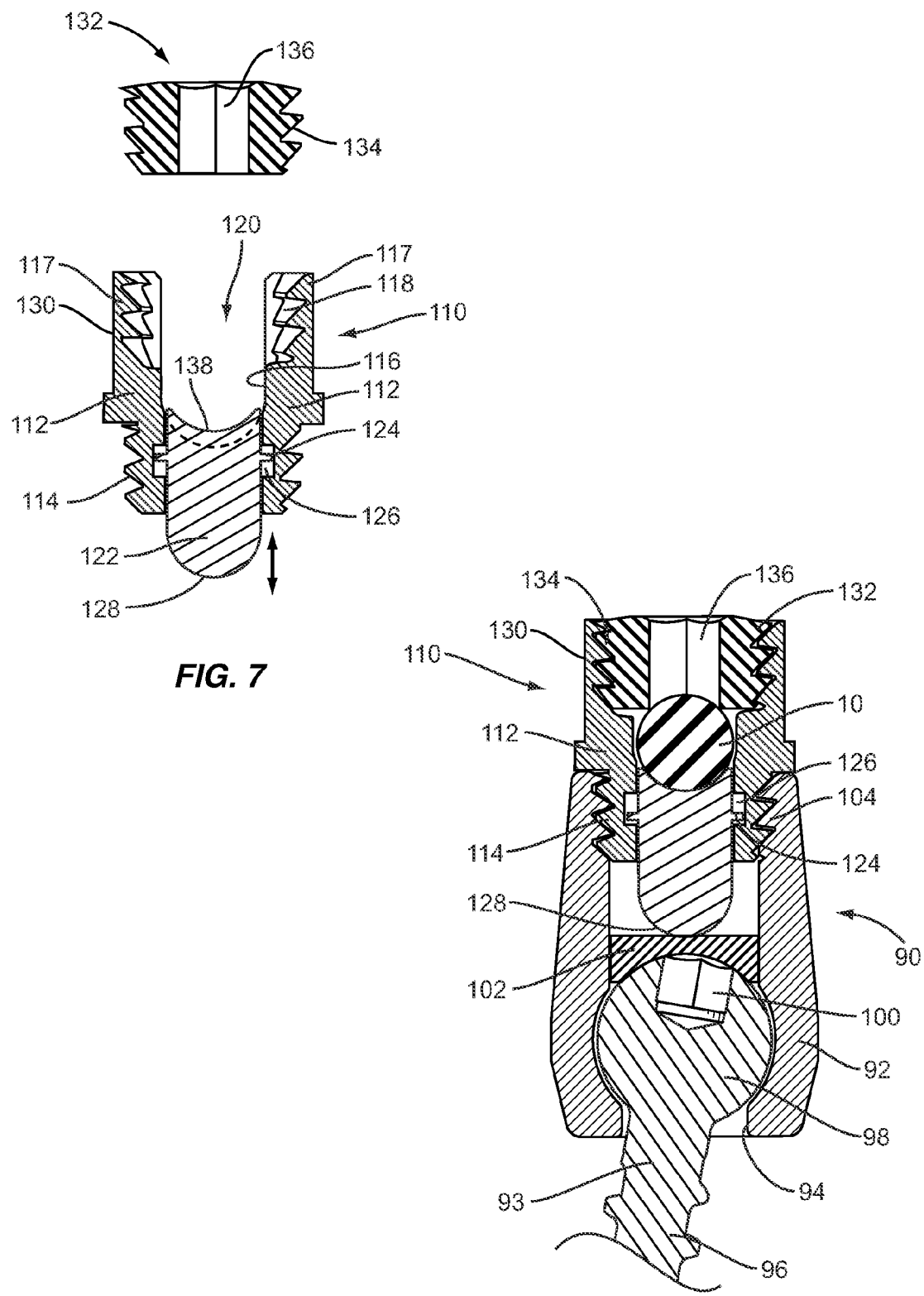
FIG. 7 is a partially exploded cross sectional view of yet another embodiment of the pedicle screw head extender of the present invention.
FIG. 8 is a side cross sectional view of a multi-axial pedicle screw with the pedicle screw head extender illustrated in FIG. 7 installed thereon with a spinal rod attached thereto.

FIGS. 7 and 8 show yet another embodiment of the pedicle screw head extender of the present invention. In this embodiment, the pedicle screw head extender 110 is connected to a multi-axial head pedicle screw 90. A multi-axial pedicle screw 90 is well known in the industry and is described above. The pedicle screw head extender 110 of the present invention is shown having a generally cylindrical body 112 with a distal portion which is externally threaded as shown at 114, and a proximally extending pair of oppositely positioned branches 117 which are internally threaded as shown at 118. A slot 116 is formed between the branches 117 for receiving a spinal rod 10 therebetween. The body 112 is provided with an axial bore 120 extending totally through the body from its proximal end to it distal end. A piston 122 is provided in the bore 120 such that a limited axial movement of the piston is allowed within the bore 120 of the body 112. The piston 122 is provided with an annular flange 124 extending about its outer periphery and this flange 124 is received within an annular groove 126 positioned within the bore 120 of the body 112. The piston 122 is positioned within the body 112 such that its distal end 128 extends below the distal threads 114 of the body 112 and has a proximal end 138 that would extend up into the slot 116. This distal end 128 may be in the shape of a spherical knob or may have other shapes as best suited for use with a multi-axial pedicle screw. The flange 124 and groove 126 act to allow a limited axial movement of the piston within the bore 120 of the body 112. The proximally extending pair of oppositely positioned branches 117 are provided with external flats 130 to allow for the use of an installation tool (i.e. a wrench or socket driver or the like) to provide installation of the pedicle screw head extender 110 onto the multi-axial pedicle screw 90. A set screw 132 is provided having external threads 1346 and an axially extending hexangular hole 136 for receiving a screw driver to allow for installation of the set screw 132 to the extender 110.

Referring to FIG. 8, the pedicle screw head extender 110 is shown in position attached to the multi-axial pedicle screw 90. The external threads 114 of the distal portion of the extender 110 are shown in engagement with the internal threads 104 of the head 92 of the multi-axial pedicle screw 90. Once fully seated within the head, the distal end 128 of the piston 122 of the extender 110 will contact the crown 102 of the pedicle screw. However, at this point the piston 122 would move back up into the bore 120 of the body 112 such that the head 92 of the multi-axial pedicle screw 90 would still be allowed to move freely with respect to the elongated stem 93. The spinal rod 10 would then be positioned within the slot 116 of the pedicle screw head extender 110 and the set screw 132 would be used to capture the rod 10 therein. The set screw 132 would contact and bias the rod 10 against the proximal end 138 of the piston 122 which in turn would bias the distal end 128 of the piston 122 against the crown 102 to lock the head 92 against any further movement with respect to the elongated stem of the pedicle screw. In this embodiment of the pedicle screw head extender, the extender 110 can be installed onto the head of the multi-axial pedicle screw 90 and still allow the head 92 of the pedicle screw to move freely about the elongated stem for easy attachment of the rod to the spinal construct. The head of the pedicle screw only becomes locked with respect to its elongated stem once the rod is properly installed within the slot 116 of the extender 110 via use of the set screw 132.

Referring now to FIG. 9, a portion of the spinal column with vertebrae V1, V2 and V3 is shown with a single rod construct like the construct in FIG. 1. However, now a pedicle screw head extender 20 is shown connected to pedicle screw 14 such that the rod 10 is fully connected to all three pedicle screws 12, 14 and 16 without unduly bending the rod or relocating vertebra V2 of the patient. Pedicle screw head extenders 40, 70, or 110 could also be shown in FIG. 9. The pedicle screws 12, 14 and 16 could be either fixed head pedicle screws or multi-axial head pedicle screws.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A spinal construct, comprising:
   a spinal screw having a threaded portion for implantation into a bone of the spine and a head portion with axially extending branches forming a slot therebetween; and
   a screw head extender comprising:
     a generally cylindrical body having a distal connection portion disposed within the slot of the screw,
     a pair of axially extending branches forming an internally threaded slot therebetween for receiving a spinal rod therein, and
     a set screw received within the internally threaded slot of the body to retain the rod within the screw head extender.

2. The spinal construct of claim 1 wherein the spinal screw is a pedicle screw.

3. The spinal construct of claim 2, wherein the pedicle screw is further provided with internal threads within the slot of the pedicle screw, the extender further having external threads provided on the distal connection portion, said distal connection portion threads being received within the internal threads of the slot of the pedicle screw.

4. The spinal construct of claim 3, wherein the pedicle screw is a fixed head pedicle screw such that the threaded portion is solidly affixed to the head portion, the extender and set screw acting to fixedly retain the rod within the internally threaded slot of the body.

5. The spinal construct of claim 3, wherein the pedicle screw is a multi-axial head pedicle screw such that the threaded portion is loosely affixed to the head portion such that the head portion is allowed to swivel about the end of the threaded portion, the extender further comprising:
   a distal axial extension extending from the distal connection portion that engages a crown positioned between the head portion and the distal axial extension to fixedly lock the head portion with respect to the threaded portion.

6. The spinal construct of claim 3, wherein the pedicle screw is a multi-axial head pedicle screw such that the threaded portion is loosely affixed to the head portion such that the head portion is allowed to swivel about the end of the threaded portion, the extender further comprising:
   an axial bore extending through the cylindrical body and communicating between the internally threaded slot and a distal end of the distal connection portion;
   a piston positioned within the axial bore for limited axial movement with respect to said body and having a distal end extending from the distal end of said body and a proximal end extending into the slot of said body such that the piston contacts the pedicle screw but does not prevent continued movement between the head portion and threaded portion of the pedicle screw; and
   whereas upon insertion of the rod and set screw within the slot of said body to fixedly retain the rod to the pedicle screw head extender, the rod biases the piston against the pedicle screw to prevent further movement between the head portion and threaded portion of the pedicle screw.

7. The spinal construct of claim 6, further comprising:
   an annular groove provided within the axial bore of the cylindrical body; and
   an annular flange extending about the piston such that the piston flange is retained within the annular groove of the cylindrical body to allow for limited axial movement of the piston with respect to the axial bore of the cylindrical body.

8. The spinal construct of claim 1, wherein the distal connection portion is provided with a plurality of concentric rings that engage an inner surface of the screw that defines the slot of the screw such that the extender is snap fitted into the slot of the screw.

9. The spinal construct of claim 1, wherein the cylindrical body has a determined axial length to allow for the measured connection between a pedicle screw implanted within the pedicle of the spine and a spinal rod for use in a spinal construct; and providing a plurality of pedicle screw head extenders have a plurality of determined axial lengths to allow a surgeon user to select such plurality of pedicle screw head extenders to use to provide a connection between the pedicle screw and spinal rod.

10. A spinal construct, comprising:
    a pedicle screw having a threaded portion for implantation into a pedicle of the spine and a head portion with axially extending branches forming a slot therebetween and
    a pedicle screw head extender comprising:
      a generally cylindrical body having a distal connection portion disposed within the slot of the pedicle screw,
      a pair of axially extending branches forming an internally threaded slot therebetween for receiving a spinal rod therein, and
      a set screw received within the internally threaded slot of the body to retain the rod within the pedicle screw head extender.

11. The spinal construct of claim 10, wherein the pedicle screw is further provided with internal threads within the slot, the extender further having external threads provided on the distal connection portion, said distal connection portion threads being received within the internal threads of the slot of the pedicle screw.

12. The spinal construct of claim 11, wherein the pedicle screw is a fixed head pedicle screw such that the threaded portion is solidly affixed to the head portion, the extender and set screw acting to fixedly retain the rod within the internally threaded slot of the body.

13. The spinal construct of claim 11, wherein the pedicle screw is a multi-axial head pedicle screw such that the threaded portion is loosely affixed to the head portion such that the head portion is allowed to swivel about the end of the threaded portion, the extender further comprising:
    a distal axial extension extending from the distal connection portion that engages a crown positioned between the head portion and the distal axial extension to fixedly lock the head portion with respect to the threaded portion.

14. The spinal construct of claim 11, wherein the pedicle screw is a multi-axial head pedicle screw such that the threaded portion is loosely affixed to the head portion such that the head portion is allowed to swivel about the end of the threaded portion, the extender further comprising:

an axial bore extending through the cylindrical body and communicating between the internally threaded slot and a distal end of the distal connection portion;

a piston positioned within the axial bore for limited axial movement with respect to said body and having a distal end extending from the distal end of said body and a proximal end extending into the slot of said body such that the piston contacts the pedicle screw but does not prevent continued movement between the head portion and threaded portion of the pedicle screw; and whereas upon insertion of the rod and set screw within the slot of said body to fixedly retain the rod to the pedicle screw head extender, the rod biases the piston against the pedicle screw to prevent further movement between the head portion and threaded portion of the pedicle screw.

15. The spinal construct of claim 14, further comprising:

an annular groove provided within the axial bore of the cylindrical body; and an annular flange extending about the piston such that the piston flange is retained within the annular groove of the cylindrical body to allow for limited axial movement of the piston with respect to the axial bore of the cylindrical body.

16. A spinal construct, comprising:

a fixed head pedicle screw having a threaded portion for implantation into the pedicle of the spine and a fixed head portion with axially extending internally threaded branches forming a slot therebetween and a pedicle screw head extender comprising:
  a generally cylindrical body having a distal connection portion with external threads disposed within the internally threaded slot of the pedicle screw and a pair of proximally extending axial branches forming an internally threaded slot therebetween for receiving a spinal rod therein, and
  a set screw received within the internally threaded slot of the body to fixedly retain the rod within the pedicle screw head extender.

17. The spinal construct of claim 16, wherein the cylindrical body has a determined axial length to allowed for the measured connection between a pedicle screw implanted within the pedicle of the spine and a spinal rod for use in a spinal construct; and providing a plurality of pedicle screw head extenders have a plurality of determined axial lengths to allow a surgeon user to select such plurality of pedicle screw head extenders to use to provide a connection between the pedicle screw and spinal rod.

18. A spinal construct, comprising:

a multi-axial head pedicle screw having a threaded portion for implantation into the pedicle of the spine and a head portion which is loosely fixed to the threaded portions such that the head portion is allowed to swivel about the end of the threaded portion and the head further having axially extending internally threaded branches forming a slot therebetween; and a pedicle screw head extender comprising:
  a generally cylindrical body having an intermediate connection portion with external threads disposed within the internally threaded slot of the pedicle screw and a pair of axially extending branches forming an internally threaded slot therebetween for receiving a spinal rod therein, and
  a distal axial extension extending from the intermediate connection portion such that upon connection of the pedicle screw head extender to the multi-axial pedicle screw the distal axial extension acts to fixedly lock the head portion with respect to the threaded portion.

19. A spinal construct, comprising:

a multi-axial head pedicle screw having a threaded portion for implantation into the pedicle of the spine and a head portion which is loosely fixed to the threaded portions such that the head portion is allowed to swivel about the end of the threaded portion and the head further having axially extending internally threaded branches forming a slot therebetween; and a pedicle screw head extender comprising:
  a generally cylindrical body having a distal connection portion with external threads disposed within the internally threaded slot of the pedicle screw and a pair of axially extending branches forming an internally threaded slot therebetween for receiving a spinal rod therein,
  an axial bore extending through the cylindrical body and communicating between the slot and a distal end of the distal connection portion, and
  a piston positioned within the axial bore for limited axial movement with respect to said body and having a distal end extending from the distal end of said body and a proximal end extending into the slot of said body such that upon insertion of the pedicle screw head extender within the slot of the pedicle screw the piston contacts the pedicle screw but does not prevent continued movement between the head portion and threaded portion of the pedicle screw; and whereas upon insertion of the rod and set screw within the slot of said body to fixedly retain the rod to the pedicle screw head extender, the rod biases the piston against the pedicle screw to prevent further movement between the head portion and threaded portion of the pedicle screw.

20. The spinal construct of claim 19, wherein the cylindrical body has a determined axial length to allowed for the measured connection between a pedicle screw implanted within the pedicle of the spine and a spinal rod for use in a spinal construct; and providing a plurality of pedicle screw head extenders have a plurality of determined axial lengths to allow a surgeon user to select such plurality of pedicle screw head extenders to use to provide a connection between the pedicle screw and spinal rod.

* * * * *